US00PP35561P2

(12) United States Plant Patent
Moucheboeuf

(10) Patent No.: US PP35,561 P2
(45) Date of Patent: Dec. 26, 2023

(54) ***DIANTHUS* PLANT NAMED 'WP22 PIE39'**

(50) Latin Name: ***Dianthus allwoodii* hort.**
Varietal Denomination: WP22 PIE39

(71) Applicant: Plant Genetics International, Ltd., Exeter (GB)

(72) Inventor: Laetitia Moucheboeuf, Dawlish (GB)

(73) Assignee: PLANT GENETICS INTERNATIONAL. LTD, Exeter (GB)

( * ) Notice: Subject to any disclaimer, the term of this patent is extended or adjusted under 35 U.S.C. 154(b) by 0 days.

(21) Appl. No.: 17/979,759

(22) Filed: Nov. 3, 2022

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273, 272
CPC ..... A01H 5/0233; A01H 5/0227; A01H 5/02
See application file for complete search history.

(56) References Cited

PUBLICATIONS https://planthaven.com/plant/dianthus-american-pie-berry-a-la-mode/#:~: text=Large%20single%20blooms%20with%20timeless,Spring%2C%20repeating%20summer%20%26%20fall; Jan. 10, 2023; 3 pages.*
https://www.monrovia.com/american-pier-berry-a-la-mode-dianthus.html; Jan. 10, 2023; 2 pages.*
https://www.growertalks.com/Article/?articleid=25813; Jul. 1, 2022; 2 pages.*
chrome-extension://efaidnbmnnnibpcajpcglclefindmkaj/https://irp.cdn-website.com/42122c9a/files/uploaded/Michells-2023Catalog-sm.pdf; Jan. 10, 2023.*

* cited by examiner

*Primary Examiner* — Kent L Bell
(74) *Attorney, Agent, or Firm* — Weatherly IP Solutions, LLC; James M. Weatherly

(57) ABSTRACT

A new cultivar of *Dianthus* plant named 'WP22 PIE39' that is characterized by a compact mounding habit, large single white flowers with a vibrant magenta band, blooming from May through October, with a medium, clove like fragrance, glaucous blue green foliage, suitable for use as a flowering plant in pots and containers as well as for use as a cut flower and in bouquets, is disclosed.

2 Drawing Sheets

Genus and species: *Dianthus allwoodii* hort.
Variety denomination: 'WP22 PIE39'.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus allwoodii* hort. and will be referred to hereinafter by the cultivar name 'WP22 PIE39'.

'WP22 PIE39' is a complex hybrid plant that is the product of a long-term breeding program conducted in a cultivated area of Ashcombe Road, Dawlish, Devon, United Kingdom. 'WP22 PIE39' was selected in 2015 for its large single white flowers with a vibrant, magenta band, medium clove like fragrance and glaucous blue-green foliage.

'WP22 PIE39' arose and was selected as a seedling which resulted from the open pollination of a breeder stock *Dianthus*, grown within the inventor's stock of breeding lines. The female parent is *Dianthus* code name 'GI068' (unpatented and unreleased).

Asexual reproduction of 'WP22 PIE39' was first accomplished in 2015 in a cultivated area of Ashcombe, United Kingdom using the propagation method of shoot cuttings. 'WP22 PIE39' has been determined to be stable and reproduces true to type in successive generations of asexual propagation.

SUMMARY

The following traits have been repeatedly observed and represent the characteristics of the new *Dianthus* cultivar 'WP22 PIE39'. 'WP22 PIE39' has not been tested under all possible conditions and phenotypic differences may be observed with variations in environmental, climatic and cultural conditions, however, without any variance in genotype.

1. 'WP22 PIE39' exhibits a compact mounding habit.
2. 'WP22 PIE39' bears large single white flowers with a vibrant magenta band.
3. The petals of 'WP22 PIE39' are flat.
4. 'WP22 PIE39' blooms from May through October.
5. The flowers of 'WP22 PIE39' exhibit a medium, clove like fragrance.
6. 'WP22 PIE39' exhibits glaucous blue green foliage.
7. At maturity, the height of the foliage mound of 'WP22 PIE39' is 35 to 40 cm, and the width is 25 to 30 cm.
8. 'WP22 PIE39' is perennial and is hardy at least to minus 15° Centigrade.
9. 'WP22 PIE39' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP22 PIE39' showing colors as true as it is reasonably possible to obtain in colored reproductions of this type. Colors in the photographs may differ from the color values cited in the detailed botanical description, which accurately describe the actual colors of the new variety 'WP22 PIE39'.

Figure 1:
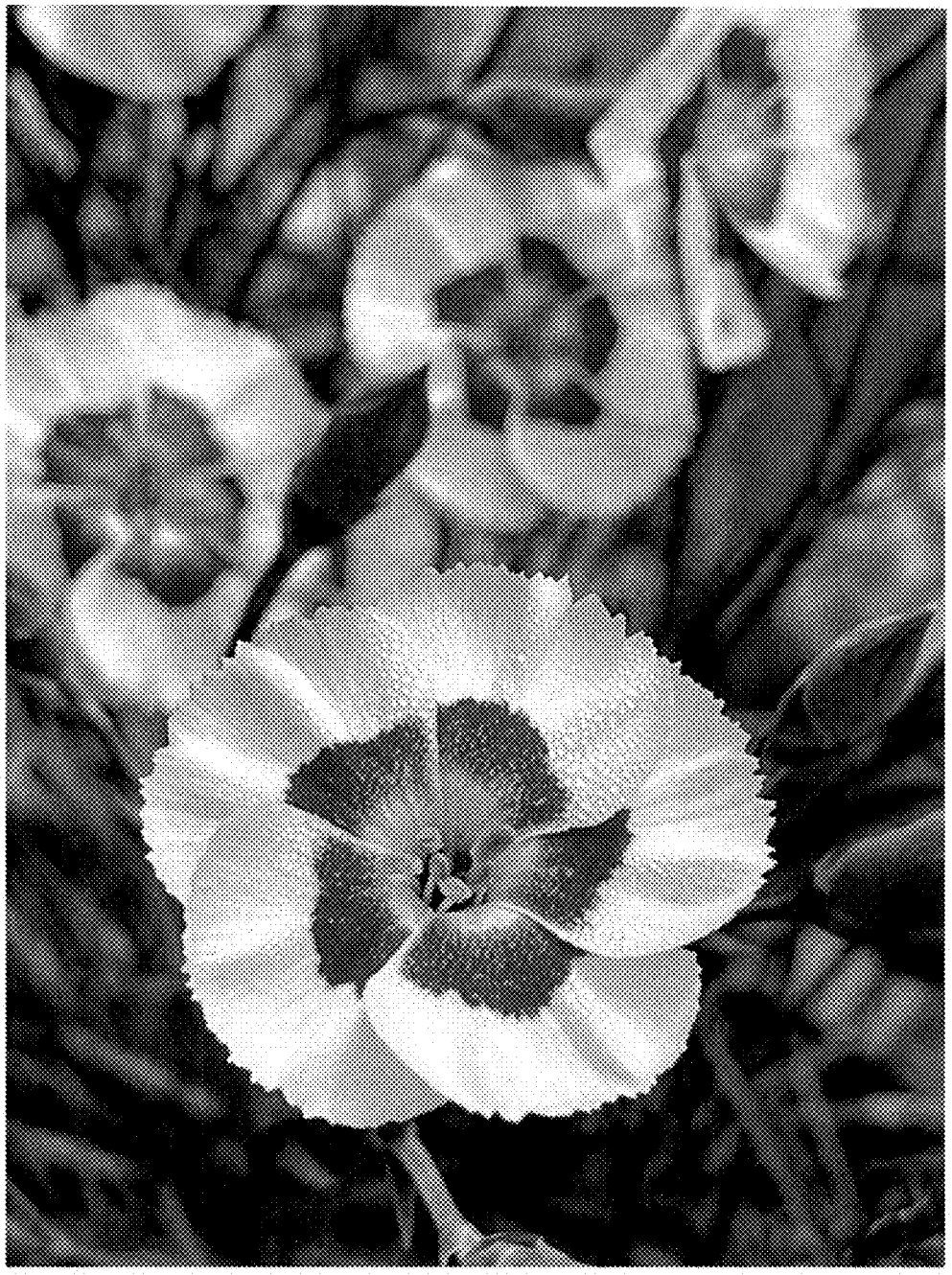
FIG. 1 depicts a close-up view of the flowers of 'WP22 PIE39'.
Figure 2:
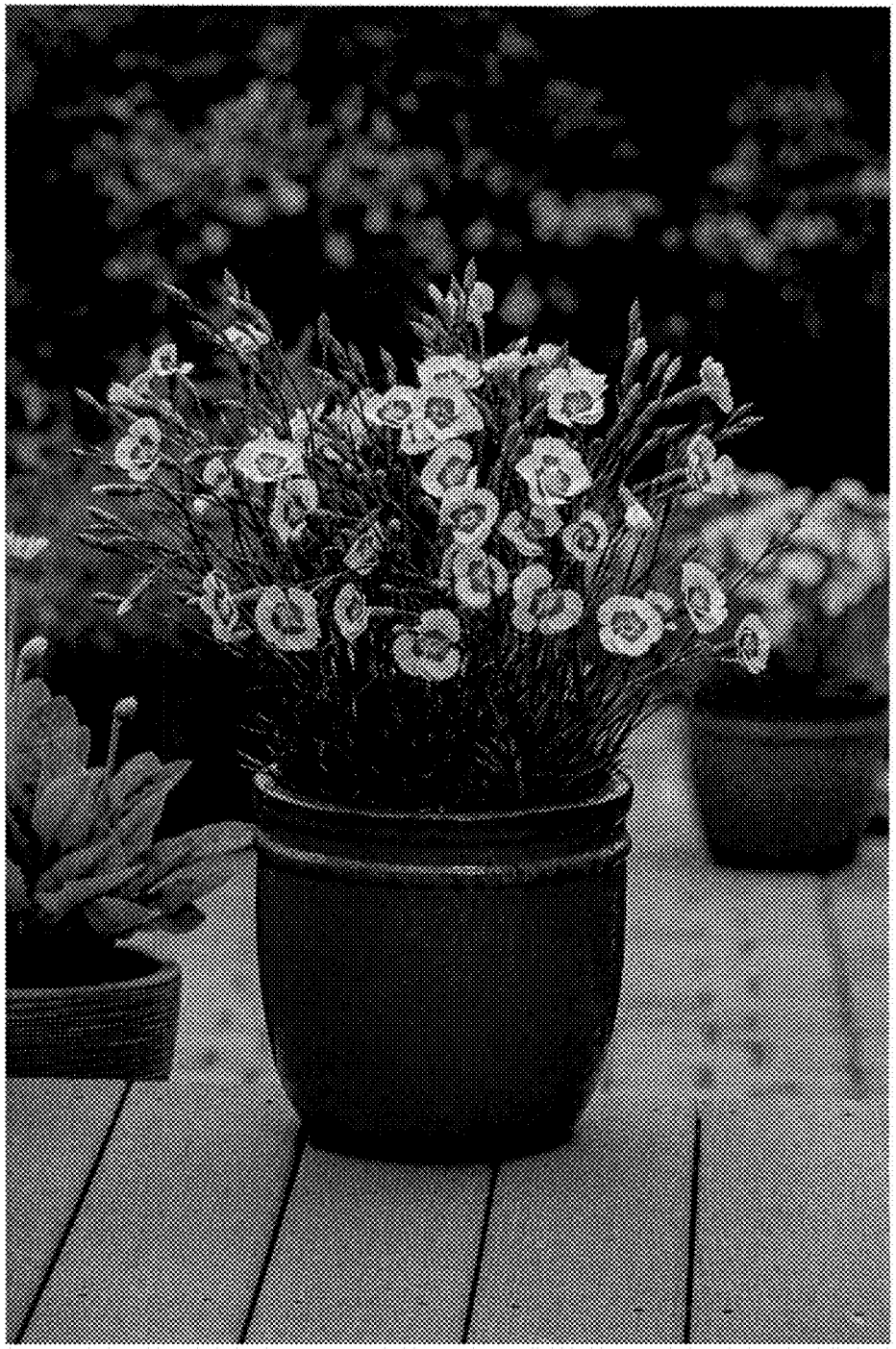
FIG. 2 depicts an entire flowering plant of 'WP22 PIE39'.

Photographs were taken in May 2021 in Santa Barbara, California of twelve-month-old plants which have been grown outdoors in 2-gallon containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP22 PIE39'. Data was collected from 12-month-old plants grown in 3-liter containers under an unheated glasshouse in Ashcombe, Dawlish, United Kingdom. The color determinations are in accordance with the sixth edition (2015) of The Royal Horticultural Society Color Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP22 PIE39'. Species: x *allwoodii*.

*Common names*.—Hybrid *Dianthus*, Garden Pink.

*Commercial classification*.—Hardy perennial.

*Use*.—Ornamental plant for pots and containers.

Parentage: 'WP22 PIE39' is a hybrid plant that resulted from the open pollination of a *Dianthus* x *allwoodii* plant.

*Female parent plant*.—'GI068' experimental *Dianthus* plant (unpatented).

*Male parent plant*.—Unknown.

Plant description:

*Bloom period*.—May to October.

*Plant habit*.—Compact mounding habit.

*Plant height*.—35 cm to 40 cm in overall height, including flower canopy.

*Plant width*.—25 cm to 30 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-litre container size from a well-rooted cutting.

Stem:

*Shape*.—Cylindrical, solid.

*Dimensions*.—11 cm in length, 5 mm diameter.

*Surface*.—Glabrous and glaucous.

*Color*.—145B, 145C and 145D (in the sheathing zone).

*Branching*.—Numerous shoots from the axils of the lower leaves.

*Internode length*.—About 5 mm between nodes (before extension of peduncle).

*Node dimensions*.—4 mm in diameter and 5 mm in length.

Leaf:

*Type*.—Evergreen.

*Dimensions*.—11 cm in length, 4 mm in width.

*Color adaxial surface*.—N189C.

*Color abaxial surface*.—N189C.

*Shape*.—Linear.

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Surfaces* (*adaxial and abaxial*).—Glaucous.

*Fragrance*.—Absent.

Flowers:

*Inflorescence*.—Simple cyme.

*Type*.—Single, polypetalous.

*Number*.—5 to 9 per stem.

*Dimensions* (*including calyx*).—40 mm in length and 45-50 mm in diameter.

*Shape*.—Circular.

*Lastingness*.—10 days at 20° Celsius on the plant; 8 to 10 days off the plant.

*Fragrance*.—Medium, clove like.

*Flowering period*.—May to October.

Peduncle:

*Shape*.—Cylindrical, solid.

*Dimensions*.—About 33 cm in length, 2 mm in diameter.

*Surface*.—Glabrous, waxy.

*Strength*.—Strong, rigid.

*Color*.—122B.

Bud:

*Shape*.—Oblong.

*Color*.—N138B to N138C on apical half and 144B to 144C on basal half (below the bracts).

*Anthocyanin*.—Absent.

*Dimensions*.—30 mm in length and 8 mm in width (at breaking color point).

Petals:

*Corolla*.—Upper and lower part of corolla is flat.

*Petal arrangement*.—Persistent, apopetalous and overlapping.

*Margin*.—Crenate-dentate.

*Indentations*.—up to 1 mm deep.

*Texture*.—Soft.

*Type*.—Single.

*Number of petals*.—5.

*Dimensions*.—50 mm in length, 30 mm in width.

*Petal shape*.—Fan shape.

*Petal surface*.—Glabrous.

*Petal apex*.—Fan shaped, crenate-dentate.

*Petal base*.—Strap shaped, tapering towards base.

*Color pattern*.—Blade is withe, with a vibrant magenta band.

*Petal color* (*adaxial surface*).—Ground color of blade: whiter than NN155D. Color of band: NN78A and N74B are both present (about 7 mm wide) with 149D at the base of the band. Color of middle of strap: whiter than NN155D. Color of base of strap: 149D.

*Petal color* (*abaxial surface*).—Ground color of blade: whiter than NN155D. Color of middle of strap: whiter than NN155D. Color of base of strap: 149D.

Calyx:

*Dimensions.*—30 mm in length and 10 mm in width.

*Shape.*—Cylindrical and straight.

*Sepals.*—5, fused up to 8 mm below the apex.

*Sepal dimensions.*—31 mm in length and 5 mm in width.

*Apex.*—Acute.

*Base.*—Truncate.

*Color of sepals, outer surface.*—N138A to N138B on apical half and 144C to 144D on basal half (below the bracts).

*Color of sepals, inner surface.*—139D.

*Anthocyanin.*—Absent.

*Splitting.*—Not observed.

Epicalyx:

*Number of bracts.*—1 pair of 2.

*Bracts shape.*—Acute.

*Bracts dimensions.*—7 mm in length and 5 mm in width.

*Bracts color.*—N138B, N138C and 144B, 144C, 144D are all present.

*Anthocyanin.*—Absent.

*Number of bracteoles.*—1 pair of 2.

*Bracteoles shape.*—Medium acuminate.

*Bracteoles dimensions.*—10 mm in length and 10 mm in width.

*Bracteoles color.*—N138B, N138C and 144B, 144C, 144D are all present.

*Bracteoles anthocyanin.*—Absent.

Reproductive organs:

*Stamen number.*—10.

*Stamen dimensions.*—30 mm length and 0.5 mm diameter.

*Color of filaments.*—Whiter than NN155D.

*Anther number.*—10.

*Anther dimensions.*—3 mm length and 0.5 mm in diameter.

*Color of anthers.*—76A (when fresh anthers).

*Anther attachment.*—Dorsifixed.

*Pollen.*—Present, 202C.

*Style number.*—2.

*Style shoulder.*—Absent.

*Color of style.*—Whiter than NN155D.

*Style dimensions.*—30 mm to 35 mm in length and 1 mm in width. Stigma number: One on each style.

*Stigma color.*—Whiter than NN155D.

*Stigma dimensions: About* 15 mm long along the top of the style, fimbriated zone, 5 to 8 mm above petals at maturity (and curling).

*Ovary position.*—Superior.

*Ovary dimensions.*—10 mm in length and 6 mm in diameter.

*Ovary shape.*—Oblong.

*Ovary surface and texture.*—Smooth and slightly ribbed.

*Ovary color.*—144C and 145A are both present at the uppermost surface, becoming paler into 149D and 150D at the lowest surface.

Seed: No seeds have been observed.

Diseases and pests: Susceptible to known *Dianthus* pests and disease but no other susceptibilities to pests or disease are known.

COMPARISON WITH PARENTAL LINE AND KNOWN VARIETY

'WP22 PIE39' is distinguishable from the female parent as follows. The female parent 'GI068' bears light pink flowers with a maroon band. The petal edges are also deeply toothed. Also, when grown outside, the overall flowering height of 'GI068' is higher than 'WP22 PIE39'.

The variety of *Dianthus* considered to most closely resemble 'WP22 PIE39' is *Dianthus* Plant Named 'WP15 PIE41' (U.S. Plant Pat. No. 29,834). In comparison with 'WP15 PIE41', 'WP22 PIE39' bears single white flowers with a vibrant magenta band. The leaves of 'WP22 PIE39' are wider and overall, the mound is not as compact as 'WP15 PIE41'.

I claim:

1. A new and distinct cultivar of *Dianthus* plant named 'WP22 PIE39' as described and illustrated herein.

* * * * *